United States Patent [19]

Erickson et al.

[11] 4,163,004

[45] Jul. 31, 1979

[54] DENTAL FILLING MATERIALS

[75] Inventors: Wallace A. Erickson, Chicago; Byoung I. Suh, Glen Ellyn, both of Ill.

[73] Assignee: Wallace A. Erickson & Company, Chicago, Ill.

[21] Appl. No.: 807,555

[22] Filed: Jun. 17, 1977

[51] Int. Cl.$^2$ ................................................. C08K 9/04
[52] U.S. Cl. .............................. 260/42.14; 106/308 Q; 106/309; 260/998.11
[58] Field of Search ....................... 260/42.14, 998.11; 106/308 Q, 309

[56] References Cited

U.S. PATENT DOCUMENTS

| | | | |
|---|---|---|---|
| 3,066,112 | 11/1962 | Bowen | 260/42.15 |
| 3,697,475 | 10/1972 | Morris et al. | 260/42.14 |
| 4,069,192 | 1/1978 | Monte et al. | 260/42.14 |
| 4,080,353 | 3/1978 | Monte et al. | 260/42.14 |

OTHER PUBLICATIONS

Ken-React Bulletin KR-0376-4, Kenrich Petrochemicals Inc., Bayonne, N.J.
Ken-React Bulletin KR-1076-5, Kenrich Petrochemicals Inc., Bayonne, N.J.
Modern Plastics Encyclopedia, Oct. 76, vol. 53, No. 10A, pp. 161 & 166.

Primary Examiner—James H. Derrington
Attorney, Agent, or Firm—Merriam, Marshall & Bicknell

[57] ABSTRACT

An improved filler for use with a polymerizable monomer in preparing direct dental filling materials is produced by treating a finely divided inorganic filler with a tetra (alkenyloxy) titanium di(dialkyl) phosphite.

7 Claims, No Drawings

DENTAL FILLING MATERIALS

This invention relates to an improved inorganic filler material for use with a polymerizable monomer in preparing direct dental filling materials, and to a process for preparing the same.

BACKGROUND OF THE INVENTION

Direct dental filling materials consisting of a resin binder and a finely divided inorganic filler are well known to those skilled in the arts. Since the disclosure of such materials in Bowen U.S. Pat. No. 3,066,112, variations and improvements thereon have been disclosed by others, e.g. Gander et al. U.S. Pat. No. 3,385,090 and Lee et al. U.S. Pat. No. 3,926,906.

The direct filling materials to which the present invention pertains employ a resin binder system comprising a polyfunctional monomer having at least two acrylic end groups, as exemplified by 2,2-bis[4-(3-methacryloxy-2-hydroxy-propoxy)-phenyl]-propane (BIS-GMA) and the other monomeric materials taught by the above-identified references, the disclosures of which are hereby incorporated by reference. Also preferably included in the resin system are other active monomers referred to by Bowen as reactive diluents, the function of which is to reduce the viscosity of the resin binder system.

For use as dental filling materials, the resin binders are mixed with a large proportion (generally 65% by weight or more) of a finely divided inorganic filler material having a particle size within the range of about 1 to 85 microns. There is also added to the mixture of the resin binder and the inorganic filler, an appropriate quantity of a free radical generating catalyst, such as benzoyl peroxide, and a suitable activator, such as N,N-di-methyl-para-toluidine. The free radicals which are generated by the combination of the catalyst and the activator lead to rapid polymerization of the resin binder system, producing a dental filling material which has a desirable combination of properties, including high stiffness high compressive strength, low shrinkage on hardening and a low coefficient of thermal expansion, as is known by those skilled in the art.

In preparing direct filling materials of this type, as heretofore known, it has been conventional to treat the finely divided inorganic filler material with an ethyleneically unsaturated organosilane coupling or keying agent. The keying or coupling agent improves the bond between the resin binder and the inorganic filler material, thereby rendering the filler hydrophobic and increasing the strength of the cured dental filling material.

BRIEF DESCRIPTION OF THE INVENTION

In accordance with the invention it has been found that direct dental filling materials can be immproved by treating the filler material with a titanate keying or coupling agent of a type more fully defined hereinafter, instead of the organosilane heretofore used. The titanate coupling agent used in accordance with the invention is a tetra (alkenyloxy) titanium di(di-alkyl) phosphite and more specifically a compound having the general formula $(R_1O)_4—Ti—[P(OH)(OR_2)_2]_2$ where $R_1$ is an organic radical having the formula $—A—(XB)n$ in which A is a straight or branched chain, divalent or trivalent, hydrocarbon radical having 3 to 8, and preferably 6-8, carbon atoms; X is $—O—$ or

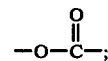

B is a straight or branched chain hydrocarbon radical having at least one terminal double bond and 3 to 8, and preferably 4 to 6, carbon atoms when X is $—O—$, or 2 to 7, preferably 3 to 5, carbon atoms when X is $$-O-\overset{\overset{\displaystyle O}{\|}}{C}-;$$

n is 1 or 2; and $R_2$ is a straight or branched chain alkyl group having 6 to 16, and preferably 10-14, carbon atoms.

The invention also comprises as one of its aspects a method for treating finely divided inorganic filler materials with a titanate coupling agent in order to improve the shelf life of a dental filling paste material including the same together with a polymerization catalyst.

Among the specific methods for practicing the invention disclosed by Bowen is the use of a two-paste system, as taught in U.S. Pat. No. 3,926,906, according to which a dentist is supplied with two pastes, equal quantities of which are mixed together immediately prior to filling a dental cavity. Each paste comprises a mixture of an appropriate resin binder, such as BIS-GMA with added diluent monomers, and a finely divided inorganic filler material treated with a keying agent, heretofore an organosilane. One of the pastes (the catalyst paste) contains an appropriate quantity of a polymerization catalyst, e.g. benzoyl peroxide, while the other paste (the base paste) contains an appropriate quantity of a promoter for the catalyst, e.g., N,N-di-methyl-paratoluidine. Although in the absence of the promoter, the catalyst alone is expected to be unable to catalyze the polymerization of the resin, thus permitting extended shelf life for the catalyst paste, it has been found that the titanate keying agents of the present invention appear to have a tendency to initiate the generation of free radicals by the catalyst and thus have an adverse effect on the shelf life of a paste containing the catalyst, even in the absence of the promoter. In accordance with the invention it has been found that by a suitable heat treatment, it is possible to deactivate the titanate-treated filler so that it has no adverse effect on the stability of the catalyst paste in extended storage.

DETAILED DESCRIPTION OF THE INVENTION

As previously described, the present invention provides an improved treated inorganic filler material for use in conjunction with known monomeric resin binders to produce a direct dental filling material. The resin binders useful in the invention can be generically described as polyfunctional monomers having at least two acrylic end groups. A preferred group of resin binders includes those having a backbone structure including at least one aromatic ring, and particularly those derived from bis phenol A by reaction with glycidyl methacrylate (BIS-GMA) or glycidyl acrylate. Other resin binders which can be used are acrylic or methacrylic esters of an aliphatic diol or triol, e.g., as disclosed in U.S. Pat. No. 3,835,090. Mixtures of these binders can also be used, as will be apparent to those skilled in the art.

Because of the high viscosity of some monomers useful in resin binders, e.g., BIS-GMA, it is usually desirable to incorporate in the resin binder a reactive diluent monomer such as methyl methacrylate or ethylene glycol dimethacrylate or the like. Typically, a suitable resin binder may contain about 70% or more of the bis-phenol A or other backbone monomer, with the remainder being one or more of the reactive diluent monomers in accordance with principles known to those skilled in the art.

The reactive resin binder is caused to polymerize by the joint action of a free radical generating catalyst, such as benzoyl peroxide, and an activator, such as N,N-di-methyl-para-toluidine or para-toluenesulfinic acid. Other similar free radical generating catalysts and promoters therefor can also be used in accordance with the principles known to those skilled in the art. The concentration of the catalyst and the promoter in the resin binder will depend on the particular identity of each and on the desired working time between the mixing of the catalyst, the promoter and the resin until the final curing of the dental material. In general, a concentration of promoter within the range of about 0.1 to about 2% by weight of the resin-filler system will be suitable, while a catalyst such as benzoyl peroxide will usually be found useful in the range of about 1% to 2%.

In general, the identity and concentrations of the backbone monomer, the diluent monomers, the catalyst and the promoter, do not, per se, form any portion of the novel aspect of the present invention.

As is customary with direct dental filling materials of the type with which the present invention is concerned, the reactive resin binder system is mixed with a finely divided inorganic filler to provide a paste-like material, the amount of filler therein being at least 50% by weight, desirably at least 65% by weight, and preferably 70% or more by weight. Suitable inorganic fillers include quartz, fused silica, glass, aluminum oxide, lithium aluminum silicate, and the like, having particle sizes ranging from sub-micron to 85 microns or more, and preferably within the range of about 1 to 75 microns.

In accordance with the invention, prior to being mixed with the resin binder to form a paste-like filling material, the inorganic filler materials are treated with a titanate keying agent which not only renders the filler particles desirably hydrophobic, but also increases the ultimate strength of the cured polymerized material by forming stable chemical bonds with both the resin binder and the surface of the filler particles. The titanate agent which are useful in the invention can be represented by the general formula $(R_1O)_4—Ti—[P(OH)(OR_2)_2]_2$ where $R_1$ is an organic radical having the formula $—A—(XB)_n$ in which A is a straight of branched chain, divalent or trivalent, hydrocarbon radical having 3 to 8 carbon atoms;

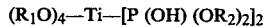
X is —O— or —O—C—;

B is a straight or branched chain hydrocarbon radical having at least one terminal double bond, 3 to 8, and preferably 4 to 6, carbon atoms when X is —O—, or 2 to 7, preferably 3 to 5, carbon atoms when X is

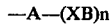
—O—C—;

n is 1 or 2; and $R_2$ is a straight or branched chain alkyl group having 6 to 16, and preferably 10–14, carbon atoms.

Examples of the $R_1O$ group as defined above include 4-allyloxy-2-isohexyloxy, 1,3-diallyloxy-2-propoxy, 1,3-dimethyacryloxy-2-propoxy, and 2,2-diallyloxymethyl-1-butoxy. Examples of the radical $R_2$ include octyl, lauryl (dodecyl), tridecyl, and palmityl (cetyl).

A particularly preferred titanate keying agent is tetra (2,2-diallyloxymethyl-1-butoxy) titanium di (di-tridecyl) phosphite.

The titanium-based keying agents of the invention can be made by transesterification of tetra-isopropoxy titanate, or other similar starting material, with $R_1OH$ to produce $(R_1O)_4$—Ti followed by reaction with the appropriate di-alkoxy phosphite.

The finely divided inorganic filler material is treated with the titanate keying agent in accordance with the invention by contacting the filler with a solution of the keying agent in a suitable organic solvent, preferably one having a relatively low boiling point permitting it to be readily evaporated, such as hexane, heptane, benzene or toluene. The concentration of keying agent in the solution is not critical, but there should be available in the solution a sufficient quantity of keying agent to react with the active centers on the filler, producing in effect a monomolecular layer of the keying agent on the filler. A volume of solvent sufficient to cover the filler material and containing about 0.5% to 1.0% by weight (based on the filler) of the keying agent will generally be sufficient.

The inorganic filler is stirred in contact with the solution of keying agent for a time on the order of 0.5–1.0 hours or more at room temperature, sufficient for the reaction between the keying agent and the filler to occur. The mixture is then filtered to remove excess solution and the filler is heated to a temperature above about 100°–105° C. to evaporate the residual solvent.

If the titanate-treated filler is intended to be used in making a catalyst paste, i.e., a mixture including resin binder and a catalyst for the polymerization thereof, for which an extended shelf life is desired, it is preferred to continue the heating of the treated filler at a temperature of about 110°–130° C. for a period of at least 4 hours, a time substantially longer than that necessary merely to evaporate the solvent. It has been found that the extended heating period serves to eliminate a tendency of the titanate in the treated filler to act as a promoter in the presence of the catalyst, which, unless the heat treatment described is employed, substantially reduces the shelf-life of a catalyst paste as a result of premature or unwanted polymerization.

The invention is illustrated by the following example.

EXAMPLE

A 3 kg quantity of finely divided (1–75 micron) quartz is added to a solution of 30g. of tetra (2,2-diallyloxymethyl-1-butoxyl titanium di(di-tridecyl) phosphite dissolved in 1.5 liter of hexane. The mixture is stirred at room temperature for 1 hour. Excess solution is removed by filtration and the filler material is heated in a vented oven for 4 hours at 110°–120° C. After cooling, the treated filler is suitable for use in direct dental filling materials in conventional fashion.

In comparison with silane treated conventional fillers, the titanate-treated filler produces direct dental filler materials which are in every significant respect (strength, hardness, stiffness, coefficient of expansion, shringkage, etc.) equal to or better than those containing conventional silane-treated fillers. Treatment with a titanate keying agent in accordance with the invention is superior to that with an organosilane following conventional practice in that treatment is simpler or more easily accomplished. Silane treatment, which is carried out in an aqueous system, requires hydrolysis of the silane. On drying of the silane-treated filler, the material is no longer a free-flowing, easily handled powder, but rather a hard, relatively coarse cake which must be reground before use. By contrast, the titanate keying agents of the invention are used as solutions in non-aqueous solvents, and require no hydrolysis. In addition, after heating to remove the solvent, the treated filler remains as a free-flowing powder which can be used without further processing.

The foregoing detailed description has been given for clearness of understanding only, and no unnecessary limitaions should be understood therefrom, as modifications will be obvious to those skilled in the art.

What is claimed is:

1. A process for treating a finely divided inorganic filler for improving its bonding properties to an active polyfunctional polymerizable monomer having at least two acrylic end groups, which method comprises treating said finely divided inorganic filler with a solution of a tetra (alkenyloxy) titanium di (di-alkyl) phosphite having the formula $$(R_1O)_4-Ti-[P(OH)(OR_2)_2]_2$$

wherein $R_1$ is an organic radical having the formula
—A—(XB)n
in which

A is a straight of branched chain, divalent or trivalent, hydrocarbon radical having 3 to 8 carbon atoms;

X is —O— or $-O-\overset{\overset{\displaystyle O}{\|}}{C}-$;

B is a straight or branched chain hyrocarbon radical having at least one terminal double bond and 3 to 8 carbon atoms when X is —O—, or 2 to 7 carbon atoms when X is $-O-\overset{\overset{\displaystyle O}{\|}}{C}-$;

n is 1 or 2; and $R_2$ is a straight or branched chain alkyl group having 6 to 16 carbon atoms;

removing excess solution; and heating said filler at a temperature of about 110°–130° C. for a period sufficient to improve the shelf life of a mixture of said monomer, said filler, and a free radical generating catalyst suitable for polymerizing said monomer.

2. The process of claim 1 wherein said heating is carried out for at least 4 hours.

3. A finely divided inorganic filler material which has been treated in accordance with claim 2.

4. An activatable paste-like material for use in producing a direct dental filling material comprising a mixture of at least one active, polyfunctional monomer having at least two acrylic end groups, a free radical generating catalyst suitable for polymerizing said monomer, and a finely divided inorganic filler material, and filler having been pretreated in accordance with claim 1.

5. The material of claim 4 wherein A has 6–8 carbon atoms, B has 4–6 carbon atoms and $R_2$ has 10–14 carbon atoms.

6. The material of claim 4 wherein said phosphite is tetra (2,2-di-allyloxymethyl-1-butoxy) titanium di(di-tridecyl) phosphite.

7. The material of claim 4 wherein said phosphite is tetra (2,2-diallyloxymethyl-1-butoxy) titanium di(di-tridecyl) phosphite.

* * * * *